United States Patent [19]

Jacobs et al.

[11] Patent Number: 4,952,605
[45] Date of Patent: Aug. 28, 1990

[54] MANOALIDE ANALOGS

[75] Inventors: Robert S. Jacobs, Santa Barbara; D. John Faulkner, La Jolla, both of Calif.

[73] Assignee: The Regents of the University of California, Berkeley, Calif.

[21] Appl. No.: 273,263

[22] Filed: Nov. 18, 1988

Related U.S. Application Data

[63] Continuation-in-part of Ser. No. 830,994, Feb. 19, 1986, Pat. No. 4,789,749, which is a continuation-in-part of Ser. No. 621,879, Jun. 18, 1984, Pat. No. 4,616,089, which is a continuation-in-part of Ser. No. 519,853, Aug. 3, 1983, abandoned.

[51] Int. Cl.$^5$ .................. A61K 31/365; C07D 307/58
[52] U.S. Cl. ........................... 514/473; 549/313; 549/318
[58] Field of Search ............... 549/313, 294, 313, 318, 549/323, 320; 514/473, 460, 885, 886, 829, 830, 843, 471, 473

[56] References Cited

U.S. PATENT DOCUMENTS

| | | | |
|---|---|---|---|
| 4,447,445 | 5/1984 | Jacobs et al. | 424/279 |
| 4,616,089 | 10/1986 | Jacobs et al. | 549/323 |
| 4,786,651 | 11/1988 | Wheeler | 514/473 |
| 4,789,749 | 12/1988 | Jacobs et al. | 549/313 |

FOREIGN PATENT DOCUMENTS 0209274  1/1987  European Pat. Off. .............. 307/66

OTHER PUBLICATIONS

Yunker et al., *J. Amer. Chem. Soc. 100:* 307–309 (1978).
Bennett et al., *Differential Effects of Manoalide on Secreted and Intracellular Phospholipases,* Yale University, Dept. of Pharmacology, unpublished.
De Silva et al., *Tetrahedron Letters 21:* 1611–1614 (1980).
De Silva et al., *Tetrahedron Letters 33:* 3747–3150 (1981).
Glaser et al., *Fed. Proc. 45:* 580 (1986).
Glaser et al., *Inactivation of Bee Venom Phospholipase A2 by Manoalide,* University California, Santa Barbara, unpublished.
Katsumura et al., *Heterocycles 10:* 87–91 (1978).
Katsumura et al., *Tetrahedron Letters 26:* 5827–5830.
Kobayashi et al., *J. Org. Chem. 45:* 5223–5225 (1980).
Larcheveque et al., *Tetrahedron Letters 22:* 1595–1598 (1981).
Ortiz et al., *Tetrahedron Letters 47:* 4215–4218 (1976).
Sullivan et al., *Tetrahedron Letters 23:* 907–910 (1982).
Sum et al., *J. Amer. Soc. 101:* 4401–4403 (1979).
Sum et al., *Tetrahedron 37:* 303–317 (1981).
Takahashi *Synthetic Communications 6:* 331–337 (1976).

*Primary Examiner*—Glennon H. Hollrah
*Assistant Examiner*—Mark W. Russell
*Attorney, Agent, or Firm*—Irell & Manella

[57] ABSTRACT

Analogs of the marine natural product manoalide are useful in treating mammals, including humans, in need of a drug having analgesic/anti-inflammatory, immunosuppressive, and/or antiproliferative activity.

4 Claims, No Drawings

MANOALIDE ANALOGS

This invention was made with Government support under Sea Grant No. NA 80 AA-D-00120, Project No. R/MP-21, awarded by the National Oceanic & Atmospheric Administration. The Government has certain rights in this invention.

This application is a continuation-in-part of U.S. patent application Ser. No. 830,994, filed 19 Feb. 1986, now U.S. Pat. No. 4,789,749, which is a continuation-in-part of U.S. patent application Ser. No. 621,879, filed 18 June 1984, now U.S. Pat. No. 4,616,089, which is a continuation-in-part of U.S. patent application Ser. No. 519,853, filed 3 August 1983, now abandoned. These patents are incorporated herein by reference.

Background Art

Compounds isolated from a marine sponge include manoalide of the formula

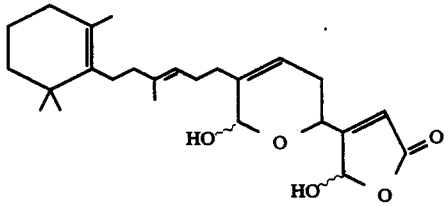

and seco-manoalide, of the formula

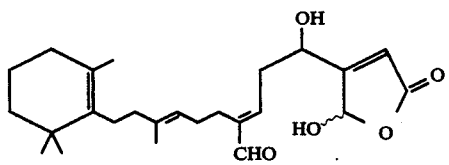

These compounds were disclosed by E. D. de Silva et al, *Tetrahedron Lett* (1981) 22:3147–3150 and *Tetrahedron Lett* (1980) 21:1611–1614. The anti-inflammatory and immunosuppressive activities of these compounds, and of an analog arising as an artifact of isolation, dehydro-seco-manoalide

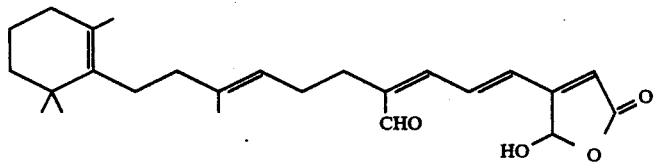

are disclosed in U.S. Pat. No. 4,447,445, application for which was filed on even date with U.S. Ser. No. 519,853.

The present invention relates to synthetic analogs of manoalide which have anti-inflammatory activities in the same range as that of manoalide, i.e., greater than that of indomethacin and less than that of hydrocortisone. Uses include treatment of rheumatoid arthritis, osteoarthritis, rheumatic carditis, autoimmune diseases such as myasthenia gravis, allergic diseases, bronchial asthma and ocular and dermal inflammatory diseases. These drugs are also useful as adjuvant therapy associated with organ and tissue transplants and, because they inhibit phospholipase $A_2$, as a local treatment for any venom in which a major constituent is the enzyme phospholipase $A_2$. In addition, manoalide analogs are immunosuppressants by virtue of their capacity to inhibit phospholipase $A_2$. Since manoalide analogs block oxazolone-induced inflammation, these compounds are useful in treating forms of allergic contact dermatitis (such as poison oak of poison ivy). They are also antiproliferative agents.

Disclosure of the Invention

The invention is directed to compounds related to the marine natural product manoalide, which are useful as anti-inflammatory agents, as immunosuppressants, and as antiproliferative agents. Thus, in one aspect, the invention relates to compounds of the formula:

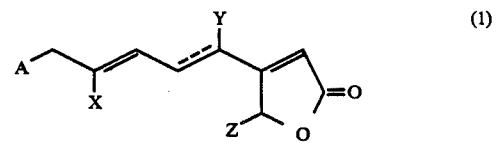

(1)

wherein X is $CH_3$, $CH_2OH$, CHO, or COOH;

the dotted line represents either a single bond or a double bond which may be in either the E or Z configuration;

Y is H or OH if — is a single bond, and is not present if — is a double bond; and;

Z is H or OH;

and wherein A is a saturated or unsaturated 3-15C hydrocarbyl group containing or not containing cyclic portions, and specifically includes

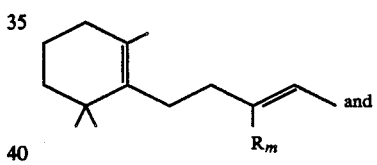

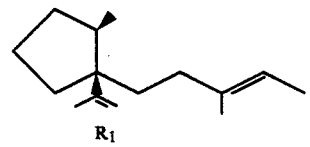

When Y is OH and X is CHO or COOH, the compound of Formula 1 includes the hemiacetal or deltalactone, respectively.

When X is COOH, the compound of Formula 1 may be in the form of the corresponding alkyl (1–6) esters), the amides, including alkyl (1–6) amides, or the pharmaceutically acceptable salts. When X is $CH_2OH$ and/or Y is OH and/or Z is OH, the compound of Formula 1 may be in the form of the acyl esters (1–6C) thereof.

Collectively these are the "pharmaceutically acceptable esters".

Certain embodiments are excluded from the compounds of the invention: those wherein A is $R_m$, X is CHO, Y and Z are OH, and —represents a single bond, and those wherein A is $R_m$, X is $CH_2OH$, Y is OH, Z is H, and —represents a single bond.

In additional aspects, the invention relates to pharmaceutical compositions containing the compounds of the invention as active ingredients, and to methods of treating inflammation, modifying unwanted immune responses, or retarding proliferation of cells using the compounds and compositions of the invention and the manoalide natural products.

Modes of Carrying Out the Invention

Description of the Preferred Embodiments

Compounds of the invention which contain alcohols may conveniently be esterified with acyl groups containing 1–6 carbon atoms using methods standard in the art. Suitable acyl groups are alkanoyl of 1–6C and alkenoyl of 3–6C and include, without limitation, acetyl, propanoyl, n-hexanoyl, 4-methylpentanoyl, and the like. The acyl groups may also be unsaturated, and thus also included are acryloyl, methyl acryloyl, 3-methyl-buten-2-oyl, and so forth.

In addition, for those embodiments wherein X is carboxyl and are not in a lactone form, the esters, amides, and salts of the free carboxyl groups are also included in the invention. Esters include those of the saturated or unsaturated alcohols, such as, for example, ethanol, n-butanol, cyclohexanol, cyclopentanol, 3-methylbuten-2-ol, i-propanol, and the like; amides include those obtained from ammonia and from alkylamines such as ethylamine, n-butylamine, hexylamine, di-isopropylamine, and so forth. Pharmaceutically acceptable salts include those formed from organic and inorganic bases.

The esters of the compounds of Formula 1 containing alcohol constituents may be prepared using standard techniques, such as treating the alcohol-containing compounds of the invention with the free acid forms of the desired acyl substituent in the presence of a strong acid such as boron trifluoride, hydrogen chloride, or sulfuric acid. (They may also be prepared from the activated forms of the acyl groups, such as the acyl chlorides.) The reaction can be carried out in an inert organic solvent in which the free acids and the alcohols are soluble, such as a hydrocarbon solvent, for example, cyclooctane, cyclohexane, or benzene, or a halogenated hydrocarbon solvent such as chloroform or dichloroethane, or an ether solvent such as diethyl ether or tetrahydrofuran. The reaction is conducted at from about 0° C. to the reflux temperature of the reaction mixture, preferably using hydrogen chloride as a catalyst at a temperature for the reaction mixture of 15° C.–35° C.

The esters of carboxyl groups contained in Formula 1, i.e., when X is COOH, are prepared in a similar manner, except using the appropriate alcohol as reagent. The amides are prepared by activation of the carboxylic acid moiety, e.g., with sulfonyl chloride, followed by treatment with the appropriate amine.

The salts are prepared by treating the free acids with an appropriate amount of pharmaceutically acceptable base, such as inorganic bases, e.g., sodium hydroxide, potassium hydroxide, ammonium hydroxide, or calcium hydroxide; or organic bases such as trimethylamine, triethylamine, 2-diethylaminoethanol, lysine, caffeine, procaine, choline, betaine, theobromine, polyamine resins, and the like. The reaction is conducted in water alone or in combination with an inert, water-miscible organic solvent, at a temperature of from about 0° C. to about 100° C., preferably at room temperature.

The salt derivatives can be reconverted to their respective free acids by acidifying said salts with an acid, preferably an inorganic acid, e.g., hydrochloric acid, at a temperature of from about 0° C. to about 50° C., preferably at room temperature.

The product is isolated by conventional means, such as dilution of the reaction mixture with water and extraction at a suitable pH with a water immiscible organic solvent.

Certain of the compounds of the invention contain chiral centers, and accordingly may be prepared as enantiomeric or diastereomeric mixtures or in optically pure form. Unless otherwise specified herein, the preparations may be racemates at each chiral center or of either of the two chiralities. However, the scope of the invention is not to be considered as limited to racemates and mixtures, but also to encompass the individual optical isomers of the compounds. Where the chiral center corresponds to a chiral center in the natural product analogs, the naturally occurring chirality is preferred.

Similarly, the double bonds may be present in the Z or E forms or mixtures thereof. However, the stereochemistry corresponding to that of the analogous natural product is preferred.

The alkyl group represented by A can be any saturated or unsaturated hydrocarbyl of 3–15C, for example, isopropyl, n-hexyl, n-hex-3-enyl, cyclohexyl methyl, 4-methylcyclohexyl methyl, 3-(4-methylcyclohexyl)-propyl, and the like. Embodiments of the alkyl group which are found in the naturally occurring or artifactually produced analogs and generally arise from the terpenoid nature of the naturally occurring compounds, as illustrated by $R_m$ and $R_1$, are preferred.

Certain embodiments of the claimed compounds are excluded from the compounds of the invention. These include manoalide, seco-manoalide, and manoalide diol.

Preferred Embodiments

The following compounds are illustrative of particularly preferred embodiments of the invention. The table below lists the substituents and, where available, the trivial names associated with these substituents. In several cases, both the open chain and cyclic forms (lactones or hemiacetals) are included. The symbols $R_m$ and $R_1$ refer to the terpenoid substituents set forth above.

TABLE 1

| A | X | Y | Z | | Trivial Name |
|---|---|---|---|---|---|
| *$R_m$ | $CH_2OH$ | OH | H | single | manoalide diol |
| $R_m$ | COOH (free acid) | OH | OH | single | — |
| $R_m$ | COOH (lactone) | OH | OH | single | manoalide delta-lactone |
| $R_m$ | CHO | — | OH | double (E) | dehydro-seco-manoalide |
| $R_m$ | CHO (hemiacetal) | OH | H | single | — |
| $R_m$ | $CH_3$ | — | OH | double (E) | — |
| $R_m$ | $CH_3$ | H | OH | single | luffariellolide |
| $R_m$ | $CH_3$ | OH | H | single | — |
| *$R_m$ | CHO | OH | OH | single | manoalide |

TABLE 1-continued

| A | X | Y | Z | | Trivial Name |
|---|---|---|---|---|---|
| *$R_m$ | CHO (hemiacetal) | OH | OH | single | seco-manoalide |
| $R_1$ | $CH_2OH$ | OH | H | single | — |
| $R_1$ | COOH (free acid) | OH | OH | single | — |
| $R_1$ | COOH (lactone) | OH | OH | single | — |
| $R_1$ | CHO | — | OH | double (E) | — |
| $R_1$ | CHO (hemiacetal) | OH | H | single | — |
| $R_1$ | $CH_3$ | — | OH | double (E) | — |
| $R_1$ | $CH_3$ | H | OH | single | — |
| $R_1$ | $CH_3$ | OH | H | single | — |
| $R_1$ | CHO (hemiacetal) | OH | OH | single | luffariellin A |
| $R_1$ | CHO | OH | OH | single | luffariellin B |
| i-butyl | $CH_2OH$ | OH | H | single | — |
| n-hexyl | COOH (free acid) | OH | OH | single | — |
| cyclohexyl methyl | COOH (lactone) | OH | OH | single | — |
| i-butyl | CHO | — | OH | double (E) | — |
| n-hexyl | CHO (hemiacetal) | OH | H | single | — |
| cyclohexyl methyl | $CH_3$ | — | OH | double (E) | — |
| i-butyl | $CH_3$ | H | OH | single | — |
| n-hexyl | $CH_3$ | OH | H | single | — |
| cyclohexyl methyl | CHO (hemiacetal) | OH | OH | single | — |
| i-butyl | CHO | OH | OH | single | — |
| n-hexyl | CHO (hemiacetal) | OH | OH | single | — |
| cyclohexyl methyl | CHO | OH | OH | single | — |

*Not compounds of the invention.

Modes of Preparation

Examples 1 and 2 below illustrate methods for conversion of manoalide by oxidation and by reduction to alternate forms.

The various embodiments of X, Y, Z, and the dotted line are related to the corresponding embodiments of manoalide or its analogs by oxidation, reduction, and dehydration. In manoalide per se, X is CHO (hemiacetal), Y is OH, Z is OH, and the dotted line represents a single bond. The conversion of manoalide to the more highly oxidized form wherein X is COOH (lactone) is illustrated in Example 1. An analogous process can be used to oxidize compounds of the invention where A is other than $R_m$. The conversion of manoalide to the reduced forms, wherein X is $CH_2OH$ and Z is H is illustrated in Example 2. Further reduction under more stringent conditions is used to convert X to $CH_3$ and/or reduce Y to H. By suitably adjusting the conditions, as is known in the art, Y and Z may be selectively reduced while the oxidation state of X is maintained. These conversions, too, are available for compounds of the invention wherein A is other than $R_m$. Finally, any compound of the invention wherein Y is OH may be converted to the corresponding compound containing a double bond at the positions represented by the dotted line by dehydration in the presence of a suitable catalyst or dehydrating agent.

In summary, the oxidation, reduction, and dehydration reactions illustrated below for manoalide and the obvious permutations thereof, are applicable to non-manoalide analogs wherein A is any substituent as defined herein.

The desired manoalide embodiments for various embodiments of A may be prepared by substituting the appropriate starting material for methyl trans-7,8-dihydro-ionyliden acetate used in the preparation of manoalide and seco-manoalide as described by S. Katsumura et al, *Tetrahedron Lett* (1985) 26:5827–5830, incorporated herein by reference. In that synthesis, the starting material of the formula

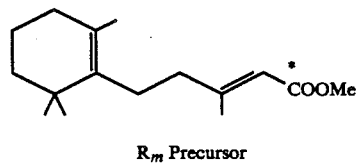

$R_m$ Precursor i.e., $R_m$ wherein the starred carbon is oxidized and esterified, is reduced with $LiAlH_4$ followed by bromination ($PBr_3$/pyridine) and this is then followed by condensation with the lithium anion of the N,N-di-methylhydrazone of pyruvaldehyde dimethylacetal to obtain a compound of the formula $R_m$—$CH_2COCH(OMe)_2$, or, more generally, A—$CH_2COCH(OMe)_2$.

The $R_1$ starting material is prepared as shown in Reaction Scheme 1, by converting 2-methylcyclopentanone to a 2-(2-methyl)cyclopentylidenylpropionate ester, e.g., through a Wittig reaction. This compound may be saponified and reduced to the corresponding alcohol. The resulting vinylic alcohol is then converted to an enol ether, for example, by reaction with acetylene under strongly basic conditions, such as sodium ethoxide. The vinylic enol ether rearranges spontaneously on heating (Claisen rearrangement) to provide 2-methyl-1-(2-propenyl)-1-(2-oxoethyl)-cyclopentane. The aldehyde may then be reduced to an alcohol, converted to a suitable leaving group (e.g., a tosylate), and reacted with a 2-butenoate ester nucleophile to form the compound below:

Reaction Scheme 1

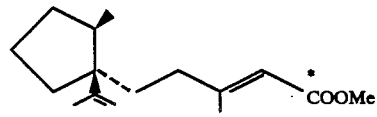

$R_1$ Precursor

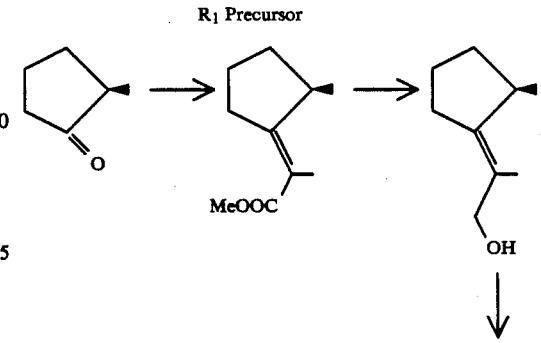

-continued
Reaction Scheme 1

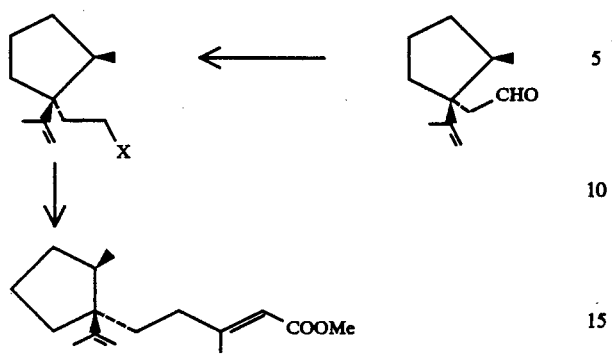

The remainder of the synthesis is summarized in Reaction Scheme 2:

jected to oxidation, reduction, or dehydration, if required, to obtain the desired derivative.

These starting materials are prepared by reacting, for example,

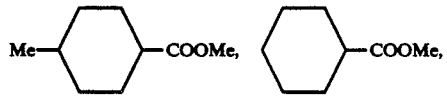

$CH_3CH=CH-COOMe$, $CH_3(CH_2)_{10}COOMe$,
$CH_3(CH_2)_6CH(CH_3)CH_2COOMe$, or 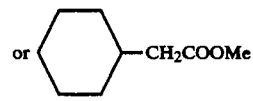

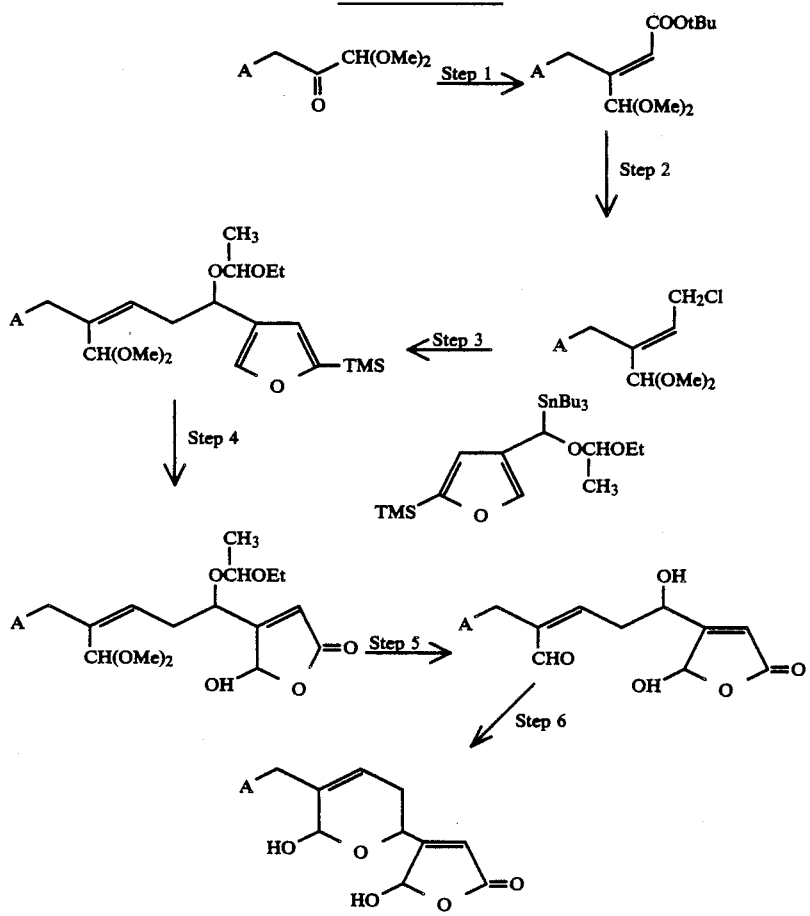

The details as to conditions and reagents used in conducting steps 1–6 are set forth in Katsumura et al (supra).

By using, in place of $R_mCH_2COCH(OMe)_2$ in Reaction Scheme 1 compounds of the formula A—CH$_2$COCH(OMe)$_2$, wherein A is, for example, R$_1$, cyclohexylmethyl, 2-butenyl, dodecanyl, 3-methyldecanyl, 2-cyclohexylethyl, or other saturated or unsaturated hydrocarbyl groups of 3–15C, the corresponding manoalide analogs can be prepared. These can be subjected in the manner described above for methyl trans-7,8-dihydro-beta-ionyliden acetate.

Utility and Administration

The compounds of the invention are shown hereinbelow to be active anti-inflammatory, immunosuppressive, and antiproliferative compounds. Accordingly, these compounds are useful in the control of inflammation, in suppressing the immune system to prevent undesirable responses, and in stemming uncontrolled proliferation, for example for treatment of hyperproliferative disorders such as psoriasis, splenomegaly, and cancer. For use in this regard, the compounds of the invention are administered to mammals, including humans, in an effective amount of 0.05 to 50 mg per day per kilogram of body weight. The amount depends, of course, on the condition to be treated, the severity of the condition, the route of administration of the drug, and the nature of the subject. The drugs may be administered orally, parenterally, or by other standard administration routes.

Parenteral administration is generally by injection, either subcutaneously, intramuscularly, or intravenously. Injectables can be prepared in conventional suspension or solution forms, as emulsions, or as solid forms suitable for reconstitution. Suitable excipients are, for example, water, saline, dextrose, Hank's solution, Ringer's solution, glycerol, and the like. In addition, the compositions may contain small amounts of nontoxic auxiliary substances, such as wetting or emulsifying agents, pH buffering agents, and so forth. Standard methods for formulating pharmaceuticals of this type may be found in *Remington's Pharmaceutical Sciences*, Mack Publishing Company, Easton, PA (latest edition).

For oral administration, suitable excipients include mannitol, lactose, starch, magnesium stearate, talcum, glucose, magnesium carbonate, and so forth. Oral compositions take the form of solutions, suspensions, tablets, pills, capsules, powders, sustained release formulations, and the like.

The following examples are intended to illustrate the invention and are not limiting. Parts and percentages are given by weight unless otherwise indicated.

EXAMPLE 1

Preparation of 3,7-Bis(hydroxymethyl)-4-hydroxy-11-methyl-13-(2,6,6-trimethylcyclohexenyl)-2,6,10-tridecatrienoic acid gamma-lactone (manoalide diol)

(A) Excess sodium borohydride (300 mg, 7.0 mM) was added in small portions to a stirred solution of manoalide (136 mg, 0.33 mM) in isopropanol (20 mL) at 0° C. The mixture was stirred at 0° C. for one hour. Excess reagent was destroyed by dropwise addition of 2% hydrochloric acid until hydrogen evolution ceased. The product was partitioned between water (100 mL) and ether (2×100 mL), the ether extract dried over sodium sulfate and then solvent removed to obtain an oil. The product was purified by HPLC to obtain the diol. Yield 75 mg (55% theoretical); oil*; $^1$H NMR (CDCl$_3$) delta 0.99 (s, 6 H), 1.60 (s, 3 H), 1.65 (s, 3 H), 4.11 (d, 1 H, J=14 Hz), 4.17 (d, 1 H, J=14 Hz), 5.39 (t, 1 H, J=7 Hz), 5.98 (br s, 1 H); HRMS. m/z 402.2770, C$_{25}$H$_{38}$O$_4$ requires 402.2770.

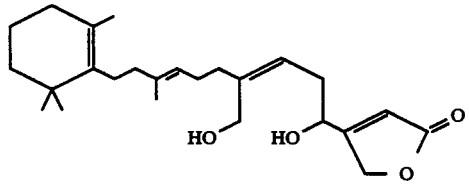

*IR(film) 3350, 1775 cm$^{-1}$
*IR(film) 3350, 1775 cm$^{-1}$ (B) Manoalide diol, as prepared in A, is dissolved in acetic anhydride in threefold molar excess in the presence of base, and the mixture stirred at room temperature for several hours. The solvents are then removed and the residue dissolved in ether and filtered to obtain a clear filtrate. Crystals of the diacetate are obtained from the filtrate. In a similar manner, but substituting for acetic anhydride the halides of the appropriate carboxylic acids, the propionate, dipropionate, hexanoate, and dipentanoate are prepared.

EXAMPLE 2

Preparation of manoalide delta-lactone

A solution of Jones's reagent (prepared from 6.7 g chromium trioxide and 6 mL sulfuric acid) was added dropwise to a stirred solution of manoalide (30 mg, 0.07 mM) in distilled acetone (20 mL) at 25° C. until the solution remained brown. After five minutes, the reaction mixture was filtered through a short column of silica gel and the solvent evaporated to obtain an oil. The product was chromatographed by HPLC to obtain the manoalide delta-lactone as a mixture of two diastereoisomers. Yield 15 mg (50% theoretical); oil*; $^1$H NMR (CDCl$_3$) delta 0.99 (s, 6 H), 1.60 (s, 3 H), 1.65 (s, 3 H), 5.10 (m, 1 H), 5.26 (dd, 0.5 H, J=12, 5 Hz), 5.37 (dd, 0.5 H, J=12, 5 Hz), 6.15 (s, 0.5 H), 6.20 (d, 0.5 H, J=7 Hz), 6.23 (s, 0.5 H), 6.35 (d, 0.5 H, J=7 Hz), 6.62 (m, 0.5 H), 6.65 (m, 0.5 H); HRMS. m/z 414.2384, C$_{25}$H$_{34}$O$_5$ requires 414.2406.

Manoalide delta-lactone is an inseparable 1:1 mixture of diastereoisomers resulting from epimerization at the hemiacetal carbon atom.

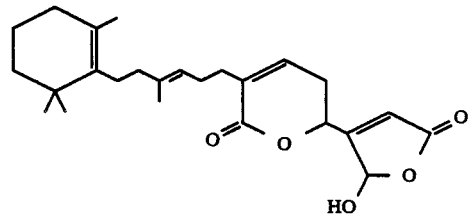

*IR(film) 3300, 1770, 1740 cm$^{-1}$; UV(MeOH) 208.5 nm (epsilon 10,350)

EXAMPLE 3

Preparation of manoalide delta-lactone acetate.

(A) Manoalide delta-lactone (15 mg, 0.04 mM) was dissolved in acetic anhydride (0.5 mL) and pyridine (1.0 mL) and the mixture was stirred at 25° C. for four hours. The solvents were removed under high vacuum and the residue dissolved in ether and filtered through a silica gel plug to obtain a clear oil. The oil was chromatographed by HPLC to obtain a mixture of diasteroisomeric acetates. Yield 16 mg (quantitative); oil;* $^1$H NMR (CDCl$_3$) delta 0.99 (s, 3 H), 1.59 (s, 3 H), 1.65 (s, 3 H), 2.18 (s, 3 H), 5.10 (t, 1 H, J=7 Hz), 5.21 (m, 1 H), 6.26 (s, 0.4 H), 6.34 (s, 0.6 H), 6.61 (m, 1 H), 6.98 (s, 1 H) HRMS. m/z 456.2514, C$_{27}$H$_{36}$O$_6$ requires 456.2512.

Manoalide delta-lactone acetate is a 6:4 mixture of two diastereoisomers. The diastereoisomers can be separated, but the material assayed was the mixture of isomers.

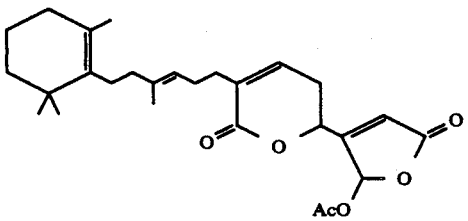

*IR(film) 1880, 1770, 1725 cm$^{-1}$; UV(MeOH) 208 nm (epsilon 10,600)

(B) In a manner similar to that set forth in A, but substituting for acetic anhydride, the anhydrides or halides of propionic, butanoic, pentanoic, or hexanoic acid, the corresponding manoalide delta-lactone propionate, butanoate, pentanoate, and hexanoate are prepared.

EXAMPLE 4

Isolation and Characterization of Dehydro-seco-manoalide

Examination of UV and $^1$H NMR data of the crude extracts of the sponge *Luffariella variabilis* provide evidence that dehydro-seco-manoalide is formed during chromatographic purification of these extracts, presumably by acid-catalyzed dehydration of manoalide on silica.

The isolation and purification of manoalide may utilize two or three chromatographic separations on silica gel. Fractions that eluted before manoalide were saved and certain fractions, distinguished by their $^1$H NMR spectra, combined. The combined fractions were chromatographed by LC on u-Porasil using diethyl ether as eluant to obtain dehydro-manoalide as a viscous yellow oil. The yield is variable.

UV (EtOH) 316 nm (epsilon 12,000), 205 nm (epsilon 10,300)

UV (EtOH+NaOH) 461 nm (epsilon 25,000), 280 nm (epsilon 1600), 246 (epsilon 2000)

IR (CHCl$_3$) 1745 cm$^{-1}$, 1670 cm$^{-1}$ $^1$H NMR (CDCl$_3$) delta 0.96 (s, 6 H), 1.56 (s, H), 1.60 (s, 3 H), 5.11 (br t, 1 H, J=7 Hz), 6.14 (s, 1 H), 6.32 (s, 1 H), 6.82 (d, 1 H, J=15.5 Hz), 6.91 (d, 1 H, J=6 Hz), 7.34 (dd, 1 H, J=15.5, 6 Hz), 9.52 (s, 1 H). $^{13}$C NMR (CDCl$_3$) delta 194.3 (d), 171.5 (s), 160.0 (d), 146.3 (s), 145.8 (d), 137.8 (s), 136.8 (s), 133.8 (s), 128.3 (d), 126.9 (s), 121.8 (d), 119.5 (d), 97.8 (d), 40.1 (t), 39.7 (t), 34.8 (s), 32.6 (t), 29.5 (t), 28.5 (q), 28.5 (q), 27.7 (t), 24.6 (t), 19.7 (q), 19.4 (t), 16.0 (q).

Mass spectrum, m/z (%), 398 (3), 380 (3), 251 (6), 137 (100).

Mass measurement, m/z=398.2429, C$_{25}$H$_{34}$O$_4$ requires 398.2457

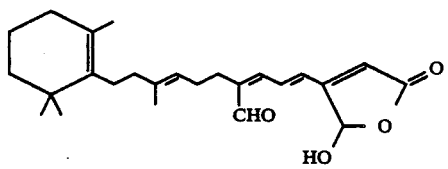

Using methods analogous to those of Example 3, B, and standard in the art, the acetate, formate, hexanoate, and pentanoate esters of dehydro-secomanoalide are prepared.

EXAMPLE 5

Isolation and Characterization of 3-(4,8-dimethyl-10-(2,6,6-trimethylcyclohexenyl)-deca,7-dienyl)-4-hydroxybutenolide (Luffariellolide)

An undescribed sponge of the genus Luffariella (voucher #85-027) was collected by hand using SCUBA (−15 to −20 m) at Palau, Western Caroline Islands in January 1985 and stored frozen. The specimen was defrosted and blended in a high-speed blender with hexane (700 mL) for 2 minutes. The resulting suspension was vigorously stirred for 30 min and then filtered Fresh hexane (700 mL) was added and the mixture was again stirred for 30 min and filtered. The combined hexane extracts were evaporated to obtain a brown oil (14.43 g). A portion of the oil was purified by chromatography on silica (MPLC) using hexanes-:EtOAc (4:1) to obtain luffariellolide as a colorless oil.

UV:(CH$_3$OH) 214 nm (epsilon 10,000), (CH$_3$OH-/OH$^-$) 253 nm (epsilon 4400);

$^1$H NMR (CDCl$_3$) delta 6.01 (br s, 1 H), 5.85 (br s, 1 H), 5.14 (br t, 2 H, J=7 Hz), 1.64 (br s, 6 H), 1.60 (br s, 3 H), 0.99 (s, 6 H); $^{13}$C NMR (CDCl$_3$) delta 171.9 (s), 169.9 (s), 136.9 (s), 136.8 (s), 136.0 (s), 126.6 (s), 123.1 (d), 121.9 (d), 117.0 (s), 99.5 (d), 40.1 (t), 39.7 (t), 39.5 (t), 34.8 (s), 32.6 (t), 28.5 (q), 27.8 (t), 27.7 (t), 26.4 (t), 24.9 (t), 19.7 (q), 19.4 (t), 16.0 (q), 15.9 (q);

High resolution mass spectrum, obsd. m/z 386.2821, C$_{25}$H$_{38}$O$_3$ requires 386.2821.

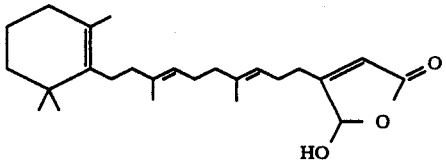

EXAMPLE 6

Isolation and Characterization of Luffariellin A and Luffariellin B

About 5% of the specimens of *Luffariella variabilis* collected at Palau during the period 9 January 1985 and 23 January 1985 contained two new compounds, luffariellin A and luffariellin B in place of the normal metabolites manoalide and secomanoalide. These specimens were identified by extracting a small portion of each specimen and analyzing the $^1$H NMR spectrum of the crude extracts.

The frozen sponge was soaked in methanol overnight, and the methanol was then decanted and filtered. This procedure was repeated 3 times. The combined extracts were evaporated, and the resulting slurry was partitioned between water and dichloromethane (5×250 mL). The combined extracts were dried over anhydrous sodium sulfate and evaporated to obtain a brown oil (670 mg). The oil was filtered through a short column of silica gel in 1:1 hexane/ethyl acetate, then chromatographed on a Lobar B silica column using 25% ethyl acetate in hexane, then 1 ethyl acetate/hexane as eluants to obtain luffariellin A (126 mg) and luffariellin B (63 mg).

Luffariellin A: oil;

IR (CHCl$_3$) 3310 (br), 1780, 1762 cm$^{-1}$;
UV (MeOH) 230 nm (4800);
$^1$H NMR (CDCl$_3$) delta 0.70 (d, 3 H, J=7 Hz), 1.59 (s, 3 H), 1.68 (s, 3 H), 4.64 (s, 1 H), 4.82 (s, 1 H), 4.85 (m, 1 H), 5.09 (br t, 1 H, J=7 Hz), 5.34 (s, 1 H), 5.70 (s, 1 H), 6.08 (s, 1 H); $^{13}$C NMR (CDCl$_3$) delta 172.0/171.8 (s), 169.0/168.3 (s), 148.0 (s), 137.2/137.0 (s), 136.7 (s), 122.6 (d), 120.9/120.6 (d), 117.8/116.7 (d), 111.6 (t), 98.3/97.8 (d), 91.3/91.1 (d), 63.1/62.3 (d), 55.1 (s), 41.8 (d), 39.6/39.4 (t), 34.8 (t), 34.3 (t), 32.4 (t), 31.0 (t), 29.4 (t), 25.9 (t), 20.7 (t), 20.7 (q), 18.1 (q), 16.2 (q);

Mass spectrum, m/z 398 (M—H$_2$O).

Luffariellin B: oil;
IR (CHCl$_3$) 3350 (br), 1762, 1686 cm$^{-1}$;
UV (MeOH) 226 nm (10,000);
$^1$H NMR (CDCl$_3$) delta 0.70 (d, 3 H, J=7 Hz), 1.55 (s, 3 H) 1.67 (s, 3 H), 4.63 (s, 1 H), 4.82 (s, 1 H), 5.07 (br t, 1 H, J=7 Hz), 5.40 (m, 1 H), 6.11 (br s, 2 H), 6.56 (t, 1 H, J=7 Hz), 9.40 (s, 1 H); $^{13}$C NMR (CDCl$_3$) delta 195.2 (d), 171.2 (s), 170.4/30 169.3 (s), 148.3/148.2 (s), 145.7/145.6 (d), 137.4 (s), 122.2 (d), 118.3 (d), 117.7 (t), 98.3/97.9 (d), 66.8/66.3 (d), 55.1 (s), 41.9 (d), 34.8 (2C, t), 31.0 (t), 29.1 (t), 26.8 (t), 24.5 (t), 20.7 (t), 20.7 (q), 18.1 (a), 16.3 (q);

MS m/z 398 (M—H$_2$O).

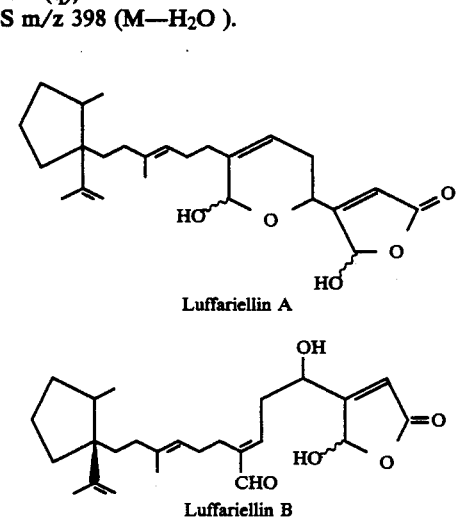

Luffariellin A

Luffariellin B

EXAMPLE 7

Mouse Ear Anti-Inflammatory Assay

Test compound and phorbol myristate acetate (PMA) are topically applied simultaneously to the pinnae of the left ears of mice. PMA alone is applied to the right ear. Three hours and 20 minutes after application, the mice are sacrificed, left and right ears removed, and standard sized bores taken. Edema (inflammation) is measured as the difference in weight between left and right ears (C. G. Van Arman, Clin Pharmacol Ther (1974) 16:900–904).

The results of separate, similar experiments are set forth below (*=statistically significant difference).

In the determinations of Table 2, PMA was at 1.5 ug/ear; the average weight of an untreated mouse ear is 9.3 mg (100% inhibition) and the average weight of an ear treated with PMA alone is 23 mg (0% inhibition).

TABLE 2

| Compound | Dose (ug/ear) | Average Ear Weight (mg/ear) |
|---|---|---|
| Manoalide | 7.5 | 20.45 |

TABLE 2-continued

| Compound | Dose (ug/ear) | Average Ear Weight (mg/ear) |
|---|---|---|
|  | 10.0 | 19.75 |
|  | 20.0 | 17.00* |
|  | 40.0 | 16.80* |
|  | 80.0 | 12.90* |
|  | 160.0 | 12.60* |
|  | 320.0 | 11.20* |
| Manoalide Diol | 25.0 | 14.54* |
|  | 50.0 | 13.17* |
| Manoalide delta Lactone | 25.0 | 16.28* |
|  | 50.0 | 14.87* |
| Manoalide delta Lactone Acetate | 25.0 | 16.64* |
|  | 50.0 | 13.34* |

In another separate experiment, the effect of dehydro-seco-manoalide was determined (PMA=15 μg/ear).

TABLE 3

| Agent | ug/ear | Average Ear Weight (mg/ear) |
|---|---|---|
| None | — | 24.60 |
| Dehydro-seco-manoalide | 50 | 14.30 |

TABLE 2

| Compound | Dose (ug/ear) | Average Ear Weight (mg/ear) |
|---|---|---|
| Manoalide | 7.5 | 20.45 |
|  | 10.0 | 19.75 |
|  | 20.0 | 17.00* |
|  | 40.0 | 16.80* |
|  | 80.0 | 12.90* |
|  | 160.0 | 12.60* |
|  | 320.0 | 11.20* |
| Manoalide Diol | 25.0 | 14.54* |
|  | 50.0 | 13.17* |
| Manoalide delta Lactone | 25.0 | 16.28* |
|  | 50.0 | 14.87* |
| Manoalide delta Lactone Acetate | 25.0 | 16.64* |
|  | 50.0 | 13.34* |

Analysis of dose/response data shows that the relative potency of dehydro-seco-manoalide to manoalide itself is 1.32.

In separate, similar experiments, where PNA was at 1.5 ug/ear, luffariellin A and B (50 ug/ear) gave statistically significant differences in relative increase in ear weight (0.308±0.065 and 0.262±0.053, respectively) as compared to PNA alone (0.618± 0.113); as did 50 ug luffariellolide (0.221±0.068) as compared to PMA alone (0.929±0.200).

EXAMPLE 8

Inhibition of Phospholipase A

The effect of the compounds of the invention bee venom phospholipase A$_2$ (PLA$_2$) was compared with the inhibition of this enzyme by manoalide.

In one assay using standard assay conditions of pH 7.4, 41° C., 1.36 mM phosphatidylcholine (dipalmitoyl), 2.76 mM Triton X-100, and 1.0 mM Ca$^{+2}$, and measuring phospholipase A$_2$ activity by Radiometer pH stat, the following results were obtained.

TABLE 4

| | (Percent Inhibition) | |
|---|---|---|
| Conc uM | Manoalide | Dehydro-seco-manoalide |
| 0.25 | 20.7 | 30.3 |

TABLE 4-continued

| | (Percent Inhibition) | |
|---|---|---|
| Conc uM | Manoalide | Dehydro-seco-manoalide |
| 0.50 | 48.0 | 61.8 |
| 0.75 | 73.5 | 51.3 |
| 2.00 | 92.8 | 72.4 |
| 4.00 | 94.5 | 87.3 |

An alternative assay uses labeled substrate as described below.

Unlabeled dipalmitoyl phosphatidylcholine (1.36 mM), and 2.76 mM Triton X-100, 10 mM Tris, 1 mM $CaCl_2$, pH 7.4 at 41° C. were dispersed with a Wheaton glass homogenizer and Teflon pestle and subsequently sonicated for 30 seconds to allow formation of a homogeneous monomolecular substrate. 1-palmitoyl-2-[9,10(n)$^3$H]-palmitoyl-L-3-phosphatidylcholine was added to the unlabeled phosphatidylcholine after sonication to give a final activity of 0.014 uCi per 0.5 ml substrate (12,000 cpm).

Aliquots of 0.5 ml of the labeled substrate were equilibrated at 41° C. for 10 min before addition of the enzyme. Enzyme was added to yield a final concentration of 0.495 units/ml and hydrolysis allowed to continue for 30 seconds.

The reaction was quenched and [$^3$H]-palmitic acid was extracted as follows.

The reaction was terminated by addition of 5 volumes of extraction mixture (isopropyl alcohol: n-heptane: 05M $H_2SO_4$, 40:10:1 v/v/v), and vortexed. To achieve phase separation, 4 volumes (2.0 ml) of n-heptane and 2 volumes (1.0 ml) of $H_2O$ were added and vortexed. To clarify the layers the mixture was centrifuged in an IEC clinical centrifuge at low-speed for 2 min; 1 ml of the upper heptane layer was removed and diluted in 1.0 ml of n-heptane; 100-150 mg of Silica Gel 60 HR (Merck) was added, vortexed, and centrifuged at 800× g for 5 min to pellet the silica gel. 1.0 ml of the heptane supernatant was removed, added to 10 ml of Hydrofluor scintillation cocktail, and counted in a Packard Tri-Carb liquid scintillation counter.

Final counts were corrected for normal background and for any [$^3$H]-PC coextracted with [$^3$H]-palmitic acid. Extraction efficiency was determined in control assays (without enzyme) by addition of [$^{14}$C]-palmitic acid before extraction.

The following results were obtained using luffariellolide with 0.495 units/ml bee venom $PLA_2$, pH 7.4 at 41° C.

| Conc uM | % Inhibition |
|---|---|
| 0.25 | 58.98 |
| 0.5 | 59.70 |
| 1.0 | 62.64 |

EXAMPLE 9

Effect on CHO Cell Growth

Chinese hamster ovary K1 cells are maintained in Dulbecco's Modified Eagle's Medium at 36° C. with 95% air and 5% $CO_2$. Cells are transferred into 35 mm culture dishes, allowed 24 hours to adhere, then exposed to medium containing drug for the duration of the experiment. The number of adhered cells is counted at 24, 48, and 72 hours after initial exposure to drug.

Growth was inhibited by 42 uM luffariellolide by 63% at 24 hours, 74% at 48 hours, and 71% at 72 hours.

We claim:

1. A compound of the formula:

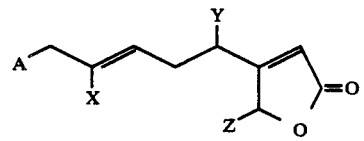

wherein
A is $R_1$ or $R_m$, wherein $R_1$ and $R_m$ are
X is $CH_3$;
Y is H;
Z is OH;
and the pharmaceutically acceptable 1-6C alkanoyl and 3-6C alkenoyl esters, and salts thereof.

2. The compound of claim 1 which is luffariellolide.

3. A method of treating mammals in need of a drug having analgesic and/or an active agent, an analgesic and/or anti-inflammatory amount of the compound of claim 1.

4. A pharmaceutical composition for alleviating pain and/or inflammation in mammals, for effecting immunosuppression in mammals, or having anti-proliferative activity in mammals, which comprises a therapeutically effective amount of a compound of claim 1 in admixture with a pharmaceutically acceptable excipient.

* * * * *